United States Patent [19]

Croughan

[11] Patent Number: 5,773,703
[45] Date of Patent: Jun. 30, 1998

[54] HERBICIDE RESISTANT RICE

[75] Inventor: Timothy P. Croughan, Crowley, La.

[73] Assignee: Board of Supervisors of Louisiana State University and Agricultural and Mechanical College, Baton Rouge, La.

[21] Appl. No.: 628,031

[22] Filed: Apr. 4, 1996

Related U.S. Application Data

[63] Continuation of Ser. No. 345,213, Nov. 28, 1994, Pat. No. 5,545,822, which is a continuation of Ser. No. 171,210, Dec. 21, 1993, abandoned, which is a continuation of Ser. No. 934,878, Aug. 21, 1992, abandoned.

[51] Int. Cl.[6] .................................................. A01H 5/00
[52] U.S. Cl. ...................... 800/235; 47/58; 800/DIG. 57
[58] Field of Search ..................................... 800/200, 235, 800/DIG. 57; 47/58

[56] References Cited

U.S. PATENT DOCUMENTS

| | | | |
|---|---|---|---|
| 4,761,373 | 8/1988 | Anderson et al. | 435/172.3 |
| 5,013,659 | 5/1991 | Bedbrock et al. | 435/172.3 |
| 5,545,822 | 8/1996 | Croughan | 800/235 |

OTHER PUBLICATIONS

Lee et al., "The Molecular Basis of Sulfonylurea Herbicide Resistance in Tobacco," The EMBO J., vol. 7, No. 5, pp. 1241–1248 (1988).

Saxena et al., "Herbicide Resistance in *Datura innoxia*," Plant Physiol., vol. 86, pp. 863–867 (1988).

Mazur et al., "Isolation and Characterization of Plant Genes Coding for Acetolactate Synthase, the Target Enzyme for Two Classes of Herbicides," Plant Physiol. vol. 85, pp. 1110–1117 (1987).

Sathasivan et al., "Nucleotide Sequence of a Mutant Acetolactate Synthase Gene from an Imidazolinone–resistant *Arabidopsis thaliana var.* Columbia," Nucleic Acids Research vol. 18, No. 8, p. 2188 (1990).

Sebastian et al., "Soybean Mutants with Increased Tolerance for Sulfonylurea Herbicides," Crop. Sci., vol. 27, pp. 948–952 (1987).

Terakawa et al., "Rice Mutant Resistant to the Herbicide Bensulfuron Methyl (BSM) by in vitro Selection," Japan. J. Breed. vol. 42, pp. 267–275 (1992).

Newhouse et al., "Mutations in corn (*Zea mays* L.) Conferring Resistance to Imidazolinone Herbicides," Theor. Appl. Genet., vol. 83, pp. 65–70 (1991).

Sathasivan et al., "Molecular Basis of Imidazolinone Herbicide Resistance in *Arabidopsis thaliana* var Columbia," Plant Physiol. vol. 97, pp. 1044–1050 (1991).

Miki et al., "Transformation of *Brassica napus* canola cultivars with *Arabidopsis thaliana* Acetohydroxyacid Synthase Genes and Analysis of Herbicide Resistance," Theor. Appl. Genet., vol. 80, pp. 449–458.

*Primary Examiner*—Douglas W. Robinson
*Assistant Examiner*—Amy J. Nelson
*Attorney, Agent, or Firm*—John H. Runnels

[57] ABSTRACT

Novel herbicide resistance has been introduced into rice plants, making the plants resistant to herbicides which normally interfere with a plant's acetohydroxyacid synthase. For the first time it is possible to selectively control the weed called "red rice" in commercial rice fields by planting rice varieties incorporating the novel herbicide resistance, and treating the field with herbicide.

18 Claims, No Drawings

HERBICIDE RESISTANT RICE

This is a continuation of application Ser. No. 08/345,213, filed Nov. 28, 1994, issued as U.S. Pat. No. 5,545,822; which is a continuation of application Ser. No. 08/171,210, filed Dec. 21, 1993, now abandoned; which is a continuation of application Ser. No. 07/934,878, filed Aug. 21, 1992, now abandoned.

This invention pertains to herbicide resistant rice and other plants, particularly to rice and other plants resistant to the herbicides imazethapyr, imazaquin, nicosulfuron, or primisulfuron, or other herbicides which interfere with the enzyme acetohydroxyacid synthase.

BACKGROUND OF THE INVENTION

The development of novel herbicide resistance in plants offers significant production and economic advantages. Rice production is frequently restricted by the prevalence of a weedy relative of rice which flourishes in commercial rice fields. The weed is commonly called "red rice," and belongs to the same species as cultivated rice (*Oryza sativa* L.). The genetic similarity of red rice and commercial rice has made herbicidal control of red rice difficult. The herbicides Ordram (molinate: S-ethyl hexahydro-1-H-azepine-1-carbothioate) and Bolero (thiobencarb: S-[(4-chlorophenyl) methyl]diethylcarbamothioate) offer partial suppression of red rice, but no herbicide which actually controls red rice can currently be used in rice fields because of the simultaneous sensitivity of commercial rice to such herbicides.

The development of a mutant commercial rice which is resistant to a herbicide effective on red rice will greatly increase the ability to control red rice infestations. Other plants, particularly other crop plants, would also benefit from resistance to herbicides used to control weeds.

Rice producers in the southern United States typically rotate rice crops with soybeans to help control red rice infestations. While this rotation is not usually desirable economically, it is frequently necessary because no herbicide is currently available to control red rice infestations selectively in commercial rice crops. During the soybean rotation, the producer has a broad range of available herbicides which may be used on red rice, so that rice may again be grown the following year. United States rice producers can lose $200–$300 per acre per year growing soybeans instead of rice, a loss affecting about 2.5 million acres annually. Additional losses in the United States estimated at $50 million per year result from the lower price paid by mills for grain shipments contaminated with red rice. Total economic losses due to red rice in southern United States rice production are estimated to be $500 to $750 million a year.

Rice producers typically use the herbicides propanil (trade name Stam) or molinate (trade name Ordram) to control weeds in rice production. Propanil has no residual activity. Molinate is toxic to fish. Neither of these herbicides controls red rice. Imazethapyr ((±)-2-[4,5-dihydro-4-methyl-4-(1-methylethyl)-5-oxo-1H-imidazol-2-yl]-5-ethyl-3-pyridinecarboxylic acid) offers an environmentally acceptable alternative to molinate, has the residual weed control activity that propanil lacks, and is a very effective herbicide on red rice. Imazethapyr also offers excellent control of other weeds important in rice production, including barnyardgrass. Barnyardgrass is a major weed in rice production, and is currently controlled with propanil or molinate. However, there are reports that barnyardgrass is developing resistance to propanil.

The herbicide Accent (nicosulfuron: 2-(((((4,6-dimethoxypyrimidin-2-yl)aminocarbonyl))aminosulfonyl))-N,N-dimethyl-3-pyridinecarboxamide) has low animal toxicity. The amount needed to control weeds is very small, typically on the order of 0.5 ounce active ingredient per acre. Accent effectively controls weeds important in rice production. Preliminary results suggest that Accent is effective in controlling red rice.

The total potential market for rice varieties which are resistant to a herbicide that can control red rice is about 5.3 million acres in the United States, and the market outside the United States is potentially much larger. World rice production occupies about 350 million acres. Red rice is a serious weed pest in rice production in Brazil, Australia, Spain, and probably in other countries as well. Imazethapyr would offer a number of advantages over currently available herbicides if it could be used in commercial rice production. Some of those advantages are long residual activity against weeds, effective control of the most important weeds in rice production, including red rice, and relative environmental acceptability. Nicosulfuron, like imazethapyr and other herbicides that inhibit acetohydroxyacid synthase, should offer similar advantages if it could be used in commercial rice production.

U.S. Pat. No. 4,761,373 describes the development of mutant herbicide-resistant maize plants through exposing tissue cultures to herbicide. The mutant maize plants were said to have an altered enzyme, namely acetohydroxyacid synthase, which conferred resistance to certain imidazolinone and sulfonamide herbicides.

Lee et al., "The Molecular Basis of Sulfonylurea Herbicide Resistance in Tobacco," The EMBO J., vol. 7, no. 5, pp. 1241–1248 (1988), describe the isolation and characterization from *Nicotiana tabacum* of mutant genes specifying herbicide resistant forms of acetolactate synthase (also known as acetohydroxyacid synthase), and the reintroduction of those genes into sensitive lines of tobacco.

Saxena et al., "Herbicide Resistance in *Datura innoxia*," Plant Physiol., vol. 86, pp. 863–867 (1988) describe several *Datura innoxia* lines resistant to sulfonylurea herbicides, some of which were also found to be cross-resistant to imidazolinone herbicides.

Mazur et al., "Isolation and Characterization of Plant Genes Coding for Acetolactate Synthase, the Target Enzyme for Two Classes of Herbicides," Plant Physiol. vol. 85, pp. 1110–1117 (1987), discuss investigations into the degree of homology among acetolactate synthases from different species.

Reference is also made to commonly-assigned U.S. patent application Ser. No. 07/657,429, filed Feb. 19, 1991, disclosing transformed plants with genetically engineered imidazolinone resistance, conferred through a gene cloned from a plant such as a mutated *Arabidopsis thaliana*. See also a related paper, Sathasivan et al., "Nucleotide Sequence of a Mutant Acetolactate Synthase Gene from an Imidazolinone-resistant *Arabidopsis thaliana* var. Columbia," Nucleic Acids Research vol. 18, no. 8, p. 2188 (1990).

SUMMARY OF THE INVENTION

In the present invention, novel herbicide resistance has been developed, and has been expressed in rice plants. The novel rice was resistant to imazethapyr, imazaquin, nicosulfuron, and primisulfuron, and is also expected to be resistant to at least some of the other herbicides which normally interfere with acetohydroxyacid synthase. In one embodiment of this invention, a resistant rice was developed through anther culture. Anther culture is a technique which can cause genetic variability among clones. The cells were not exposed to the herbicide in culture. Rather, progeny of plants grown up from the cultures were exposed to herbicide in field conditions.

DETAILED DESCRIPTION OF THE INVENTION

Traditional mutagenesis techniques had previously been tried in the inventor's research program for some four years, but had yielded no resistant strains. The resistant line was derived by conducting anther culture on the $F_2$ progeny of a backcross made by pollinating a rice plant of the variety "Lemont" with pollen from the rice variety "Mercury," followed by a backcross using pollen from this hybrid to pollinate a plant of the variety "Mercury." The resulting backcross is described as Mercury/Lemont/Mercury. Anthers collected from a plant resulting from this backcross were plated on callus induction medium, and the resulting calli were transferred to plant regeneration media. The procedures used were generally as described in Croughan and Chu, "Rice (*Oryza sativa* L.): Establishment of Callus Cultures and the Regeneration of Plants" in Bajaj (Ed.), "Biotechnology in Agriculture and Forestry," pp. 19–37 (1991), the entire disclosure of which is incorporated by reference. Several regenerated plants were produced and grown to maturity in a greenhouse to produce seed. Progeny seed were planted in an open field, and herbicide applications were made using a garden tractor-mounted spray rig.

A set of 4,193 progeny rows derived from this anther culture procedure were planted in an open field, and were sprayed with 4 ounces per acre of Pursuit (1.00 ounce active ingredient imazethapyr per acre) at the four-leaf stage of seedling development. All rows but one were injured or killed. One row showed no apparent symptoms, however. Four weeks after the initial treatment, part of the resistant row was removed from the test site as a precaution, and the entire test site was then sprayed with 8 ounces/acre Pursuit (2.00 ounce active ingredient imazethapyr per acre). This treatment was lethal to all the rows which survived the initial spraying (but in an injured state), and again induced no apparent symptoms in the resistant line.

To maximize seed production, individual plants from the resistant row were separated and transplanted at a wide spacing. All the plants proved fertile. Approximately 7 pounds of fertile seed were harvested from the resistant plants at maturity.

The resistances of these plants to several herbicides with related activities were also tested. Nine-foot-long field plots were planted with seven rows of rice per plot. The test included both nine check rice varieties, and the herbicide resistant rice line. A shielded spray boom was used to apply herbicide, spraying six of the seven rows in each plot. The four herbicides used were Pursuit (imazethapyr: (±)-2-[4,5-dihydro-4-methyl-4-(1-methylethyl)-5-oxo-1H-imidazol-2-yl]-5-ethyl-3-pyridinecarboxylic acid), Scepter (imazaquin: 2-[4,5-dihydro-4-methyl-4-(1-methylethyl)-5-oxo-1H-imidazol-2-yl]-3-quinolinecarboxylic acid), Accent (nicosulfuron: 2-(((((4,6-dimethoxypyrimidin-2-yl) aminocarbonyl)) aminosulfonyl))-N,N-dimethyl-3-pyridinecarboxamide), and Beacon (primisulfuron: 3-[4,6-bis(difluoromethoxy)-pyrimidin-2-yl]-1-(2-methoxycarbonylphenylsulfonyl)urea). The herbicidal activity of each of these herbicides is known to be due to its effect on the acetohydroxyacid synthase (AHAS) enzyme. This enzyme catalyzes the first step in the synthesis of the amino acids leucine, valine, and isoleucine. The herbicides were applied to two replicate plots for each herbicide when the rice was at the three-leaf stage of maturity. Two replicate plots of each check variety and of the resistant line were left unsprayed as controls. The Accent treatment used 0.67 ounce of product (0.50 ounce active ingredient) per acre, with 0.25% nonionic surfactant. The pursuit treatment used four ounces of product (1.00 ounce active ingredient) per acre, with 0.25% nonionic surfactant. The Scepter treatment used one pint of product (3.00 ounces active ingredient) per acre, with 0.25% nonionic surfactant. The Beacon treatment used 0.76 ounce of product (0.57 ounce active ingredient) per acre, with 0.25% nonionic surfactant. The check plots all showed extensive injury or complete death from the herbicide treatments. The herbicide resistant line showed excellent resistance to Accent, and good resistance to Scepter and Pursuit. Resistance to Beacon was lower, but still significantly greater than that of the check rice varieties. A similar test with the same rice varieties and the resistant line was conducted at the five-leaf stage of development (i.e., plants fifteen days older than in the test described above), using Accent and Pursuit at the rates given above. The check plots again showed extensive injury or complete death from the herbicide treatments. The herbicide resistant line again showed excellent resistance to Accent, and good resistance to Pursuit.

Cross-pollination of the resistant rice with established varieties through standard means will yield herbicide-resistant rice varieties and hybrids with good productivity and other commercially desirable properties.

Preliminary work has also begun on screening rice for herbicide resistance at the protoplasm level, or at the level of small colonies of protoplast-derived cells (e.g., in a semisolid medium such as agarose around which herbicide is applied). While this technique will have the advantage of screening far greater numbers of individual genomes than the method described above, the method of initially testing in the field has its own advantages. There may not always be correspondence between the biochemistry of plant cells growing in culture and the biochemistry of plants growing in field conditions.

Because red rice and commercial rice belong to the same species, the planting of a herbicide-resistant commercial rice crop entails some risk that the herbicide resistance would be transferred to red rice. However, rice is self-pollinating, and the frequency of outcrossing is low, even between immediately adjacent plants flowering in synchrony. The likelihood of transferring resistance to red rice could be minimized by breeding resistant varieties which flower significantly earlier than does red rice (e.g., using conventional breeding techniques, or by further anther culture). If a strain of red rice nevertheless does develop which is resistant to the same herbicides as the resistant commercial rice, the plants can always be treated with a broad range of other available herbicides—particularly if the resistant red rice were discovered early, before having much opportunity to propagate.

A sample of seeds from the resistant rice line was deposited with the American Type Culture Collection (ATCC), 12301 Parklawn Drive, Rockville, Md. 20852 on Aug. 20, 1992, and was assigned ATCC Accession No. 75295. This deposit was made pursuant to a contract between ATCC and the assignee of this patent application, Board of Supervisors of Louisiana State University and Agricultural and Mechanical College. The contract with ATCC provides for permanent availability of these seeds or the progeny of these seeds to the public on the issuance of the U.S. patent describing and identifying the deposit or the publication or the laying open to the public of any U.S. or foreign patent application, whichever comes first, and for availability of these seeds to one determined by the U.S. Commissioner of Patents and Trademarks to be entitled thereto according to 35 U.S.C. § 122 and the Commissioner's rules pursuant thereto (including 37 C.F.R. §§ 1.14 and 1.801 et seq., with particular reference to 886 OG 638). The assignee of the present application has agreed that if the seeds on deposit should become nonviable or be lost or destroyed when cultivated under suitable conditions, they will be promptly replaced on notification with a viable sample of the same seeds.

Because imazethapyr, imazaquin, nicosulfuron, and primisulfuron inhibit the activity of acetohydroxyacid synthase, it is expected that the herbicide resistant rice line will show resistance to other herbicides which normally inhibit this enzyme. In addition to those discussed above, such herbicides might include the following: Oust (sulfometuron), Arsenal (imazapyr), and Cadre (trade name of a herbicide manufactured by American Cyanamid; generic name imazameth; chemical name (±)-2-[4,5-dihydro-4-methyl-4-(1-methyl-ethyl)-5-oxo-1H-imidazol-2-yl]-5-methyl-3-pyridinecarboxylic acid; alternate chemical name (±)-2-(4-isopropyl-4-methyl-5-oxo-2-imidazolin-2-yl)-5-methylnicotinic acid).

As used in the claims below, unless otherwise clearly indicated by context, the term "plant" is intended to encompass plants at any stage of maturity, as well as any cells, tissues, or organs taken or derived from any such plant, including without limitation any seeds, leaves, stems, flowers, roots, single cells, gametes, anther cultures, tissue cultures, or protoplasts.

I claim:

1. A process for controlling weeds in the vicinity of a rice plant, said process comprising applying a herbicide to the weeds and to the rice plant, wherein:
    (a) the growth of the rice plant is resistant to inhibition by one or more of the following herbicides, at levels of herbicide which would normally inhibit the growth of a rice plant: imazethapyr, imazaquin, primisulfuron, nicosulfuron, or a derivative of any of these herbicides; and
    (b) the rice plant is the plant with ATCC accession number 75295; or is a mutant, recombinant, or genetically engineered derivative of the plant with ATCC accession number 75295 or of any progeny of the plant with ATCC accession number 75295; or is a plant which is the progeny of any of these plants;
    (c) the rice plant has the herbicide resistance characteristics of the plant with ATCC accession number 75295; and
    (d) the herbicide comprises imazethapyr, imazaquin, primisulfuron, nicosulfuron, or a derivative of any of these herbicides.

2. A process as recited in claim 1, wherein the plant is the plant with ATCC accession number 75295, or is any progeny of the plant with ATCC accession number 75295; and wherein the plant has the herbicide resistance characteristics of the plant with ATCC accession number 75295.

3. A process as recited in claim 1, wherein the growth of the rice plant is resistant to inhibition by imazethapyr, at levels of imazethapyr which would normally inhibit the growth of a rice plant; and wherein the herbicide comprises imazethapyr.

4. A process as recited in claim 1, wherein the growth of the rice plant is resistant to inhibition by imazaquin, at levels of imazaquin which would normally inhibit the growth of a rice plant; and wherein the herbicide comprises imazaquin.

5. A process as recited in claim 1, wherein the growth of the rice plant is resistant to inhibit-on by primisulfuron, at levels of primisulfuron which would normally inhibit the growth of a rice plant; and wherein the herbicide comprises primisulfuron.

6. A process as recited in claim 1, wherein the growth of the rice plant is resistant to inhibition by nicosulfuron, at levels of nicosulfuron which would normally inhibit the growth of a rice plant; and where the herbicide comprises nicosulfuron.

7. A process as recited in claim 2, wherein the growth of the rice plant is resistant to inhibition by imazethapyr, at levels of imazethapyr which would normally inhibit the growth of a rice plant; and wherein the herbicide comprises imazethapyr.

8. A process as recited in claim 2, wherein the growth of the rice plant is resistant to inhibition by imazaquin, at levels of imazaquin which would normally inhibit the growth of a rice plant; and wherein the herbicide comprises imazaquin.

9. A process as recited in claim 2, wherein the growth of the rice plant is resistant to inhibition by primisulfuron, at levels of primisulfuron which would normally inhibit the growth of a rice plant; and wherein the herbicide comprises primisulfuron.

10. A process as recited in claim 2, wherein the growth of the rice plant is resistant to inhibition by nicosulfuron, at levels of nicosulfuron which would normally inhibit the growth of a rice plant; and where the herbicide comprises nicosulfuron.

11. A process for controlling weeds in the vicinity of a rice plant, said process comprising applying a herbicide to the weeds and to the rice plant, wherein:
    (a) the growth of the rice plant is resistant to inhibition by one or more of the following herbicides, at levels of herbicide which would normally inhibit the growth of a rice plant: sulfometuron, imazapyr, imazameth, or a derivative of any of these herbicides; and
    (b) the rice plant is the plant with ATCC accession number 75295; or is a mutant, recombinant, or genetically engineered derivative of the plant with ATCC accession number 75295 or of any progeny of the plant with ATCC accession number 75295; or is a plant which is the progeny of any of these plants;
    (c) the rice plant has the herbicide resistance characteristics of the plant with ATCC accession number 75295;
    (d) the herbicide comprises sulfometuron, imazapyr, imazameth, or a derivative of any of these herbicides.

12. A process as recited in claim 11, wherein the growth of the rice plant is resistant to inhibition by sulfometuron, at levels of sulfometuron which would normally inhibit the growth of a rice plant; and wherein the herbicide comprises sulfometuron.

13. A process as recited in claim 11, wherein the growth of the rice plant is resistant to inhibition by imazapyr, at levels of imazapyr which would normally inhibit the growth of a rice plant; and wherein the herbicide comprises imazapyr.

14. A process as recited in claim 11, wherein the growth of the rice plant is resistant to inhibition by imazameth, at levels of imazameth which would normally inhibit the growth of a rice plant; and wherein the herbicide comprises imazameth.

15. A process as recited in claim 11, wherein the plant is the plant with ATCC accession number 75295, or is any progeny of the plant with ATCC accession number 75295; and wherein the plant has the herbicide resistance characteristics of the plant with ATCC accession number 75295.

16. A process as recited in claim 15, wherein the growth of the rice plant is resistant to inhibition by sulfometuron, at levels of sulfometuron which would normally inhibit the growth of a rice plant; and wherein the herbicide comprises sulfometuron.

17. A process as recited in claim 15, wherein the growth of the rice plant is resistant to inhibition by imazapyr, at levels of imazapyr which would normally inhibit the growth of a rice plant; and wherein the herbicide comprises imazapyr.

18. A process as recited in claim 15, wherein the growth of the rice plant is resistant to inhibition by imazameth, at levels of imazameth which would normally inhibit the growth of a rice plant; and wherein the herbicide comprises imazameth.

\* \* \* \* \*

UNITED STATES PATENT AND TRADEMARK OFFICE
CERTIFICATE OF CORRECTION

PATENT NO. : 5,773,703
DATED : June 30, 1998
INVENTOR(S) : Timothy P. Croughan

It is certified that error appears in the above-identified patent and that said Letters Patent is hereby corrected as shown below:

Title page,
Under the heading "OTHER PUBLICATIONS," the following publications should be included:

-- Wiersma *et al.*, "Isolation, Expression and Phylogenetic Inheritance of an Acetolactate Synthase Gene From Brassica napus," Mol. Gen. Genet., vol 219, pp. 413-420 (1989). --

-- Odell *et at.*, "Comparison of Increased Expression of Wild-Type and Herbicide-Resistant Acetolactate Synthase Genes in Transgenic Plants, and Indication of Postranscriptional Limitation on Enzyme Activity," Plant Physiol., vol. 94, pp. 1647-1654 (1990). --

-- Shimamoto *et al.*, "Fertile Transgenic Rice Plants Regenerated From Transformed Protoplasts," Nature, vol. 338, pp. 274-276 (1989). --

Column 3,
Line 16, "Mercury/Lemont/Mercury" should read -- Mercury//Lemont/Mercury --.

Column 4,
Line 5, "pursuit" should read -- Pursuit --.
Line 30, "protoplasm" should read -- protoplast --.

Column 5,
Line 67, (i.e., line 2 of Claim 5), "inhibit-on" should read -- inhibition --.

Signed and Sealed this

Fourth Day of December, 2001

*Attest:*

NICHOLAS P. GODICI
*Attesting Officer*     *Acting Director of the United States Patent and Trademark Office*